United States Patent [19]
Chai-Gao et al.

[11] Patent Number: 5,858,802
[45] Date of Patent: Jan. 12, 1999

[54] DEVICE INCLUDING A BIOLOGICALLY ACTIVE SUBSTANCE IMMOBILIZED ON A COVALENT NITRIDE SUBSTRATE BY A BIFUNCTIONAL COUPLING AGENT

[75] Inventors: Hui Chai-Gao, Bern; Reto Luginbühl, Spiez; Hans Sigrist, Kernenried; Nigel Skinner, Saint-Aubin; Hendrik Van Den Vlekkert, Neuchâtel, all of Switzerland

[73] Assignee: CSEM - Centre Suisse d'Electronique et de Microtechnique SA, Neuchatel, Switzerland

[21] Appl. No.: 684,458

[22] Filed: Jul. 19, 1996

[30] Foreign Application Priority Data

Jul. 19, 1995 [FR] France .................. 95 08737

[51] Int. Cl.$^6$ ................ G01N 33/551; G01N 21/00; C12Q 1/70; C12N 11/14
[52] U.S. Cl. ............... 436/524; 436/805; 436/806; 422/57; 435/5; 435/176; 435/291; 435/14; 427/508
[58] Field of Search ................ 435/5, 176, 291, 435/14; 427/508; 436/805, 806, 524; 422/57

[56] References Cited

U.S. PATENT DOCUMENTS

| | | | |
|---|---|---|---|
| 4,562,157 | 12/1985 | Lowe et al. | 435/291 |
| 5,154,808 | 10/1992 | Miyasaka et al. | 205/157.15 |
| 5,316,784 | 5/1994 | Maurer et al. | 427/2 |
| 5,431,790 | 7/1995 | Nesburn et al. | 204/157.68 |
| 5,465,151 | 11/1995 | Wybourne et al. | 356/361 |

FOREIGN PATENT DOCUMENTS 0127438  5/1984  European Pat. Off. .

OTHER PUBLICATIONS

Collioud et al. Bioconjugate Chem. 4:528–536, 1993.
Sigrist et al. Optical Engineering 34(8): 2339–2348, 1995.
Sundarababu et al. Photochemistry and Photobiology 61 (6): 540–544, 1995.
Josef Brunner Ann. Rev. Biochem. 62: 483–514, 1993.
Max Dolder et al. J. Protein Chemistry 9(4): 407–415, 1990.
Sigrist et al. J. Photochemistry and Photobiology, B: Biology 7: 277–287, 1990.
Lolliard et al., Bioconjugate Chem. 4:528–536, 1993.

*Primary Examiner*—Marian C. Knode
*Assistant Examiner*—Jay Williams

[57] ABSTRACT

The invention relates to a device including a substrate and at least one biologically active substance bound to at least a part of the surface of this substrate, which is obtained by simultaneous or sequential reaction of said substrate and of said substance with a bifunctional coupling agent in which one of the functional groups is capable of being photoactivated and generates carbenes and is used to bind the coupling agent to the inorganic substrate and the other functional group is used to bind the coupling agent to the biologically active substance, in which said substrate is a covalent inorganic nitride.

9 Claims, No Drawings

DEVICE INCLUDING A BIOLOGICALLY ACTIVE SUBSTANCE IMMOBILIZED ON A COVALENT NITRIDE SUBSTRATE BY A BIFUNCTIONAL COUPLING AGENT

BACKGROUND OF THE INVENTION

The invention relates to a device including a biologically active substance immobilized on a covalent nitride substrate by a bifunctional coupling agent.

The ability to determine quantitatively a substance or a mixture of substances in a given medium is of considerable interest in various applications such as process monitoring, quality control, the determination of pollutants in air and water, the quantitative determination of analytes in physiological fluids, the diagnosis of diseases, the histological compatibility between individuals, food duality and the like. The concentrations of substances to be measured range from molar to picomolar quantities.

There is therefore a need for fast and sensitive detection devices for this purpose.

It has become apparent in particular that it would be advantageous to have available devices in which the biologically active substance is immobilized on an inorganic substrate which is substantially inert as to physical bonding (physisorption) with molecules of said substance and which would also be capable of being incorporated into integrated electronic and/or optical devices. Such materials are lo be found among covalent nitrides such as boron nitride (BN), titanium nitrides, phosphorus nitrides such as $P_3N_5$, carbon nitrides, silicon nitrides and transition metal nitrides. Silicon nitride is particularly preferred because of its refractive index, its waveguide properties, its low optical absorption properties and its chemical inertness, which make it well-suited to applications which rely on integrated optics.

In a different technical field, that of surgical Implants or Of surgical hardware, there is a continual need for articles whose surfaces are made biologically compatible, for example in order to minimize or eliminate rejection reactions or adverse reactions of the blood (for example coagulation) in contact with implants and instruments. Although techniques of immobilization) of biologically active substances, for example heparin, are already known, there is still a need for improvements in this field. It has become apparent that nitride coatings, for example titanium nitride coatings, applied to implants or medical or surgical devices and on which an appropriate biologically active substance would be immobilized could be of interest.

SUMMARY OF THE INVENTION

The invention therefore aims to provide devices comprising a biologically active substance which is immobilized on a substrate made of covalent nitride.

DETAILED DESCRIPTION

More precisely, the invention relates to a device including a substrate and at least one biologically active substance bound to at least a part of the surface of this substrate, which is obtained by simultaneous or sequential reaction of said substrate and of said substance with a bifunctional coupling agent in which one of the functional groups is capable of being photoactivated and generates carbenes and is used to bind the coupling agent to the inorganic substrate, and the other functional group is used to bind the coupling agent to the biologically active substance, in which said substrate Is a covalent inorganic nitride.

The bifunctional coupling agent must have a functional group or several functional groups that can generate carbene radicals on exposure to light (visible or UV). Examples of such functional groups are diazirine functional groups.

The other functional group of the coupling agent must be capable of reacting with the biologically active substance, in order to bind the coupling agent to this substance.

A class of preferred coupling agents is that of homo- or heterobifunctional agents.

Homobifunctional coupling agents which are capable of being photoactivated carry, at each end of the molecule, a photosensitive functional group, preferably aryldiazirine functional groups for functionalizing covalent nitrides. The distance between the aryldiazirine functional groups which are capable of being photoactivated may, for example, range from 0.4 to 1.7 nm. These homobifunctional agents of low molecular weight may be applied to the surface and then photoactivated, or else they may be mixed with the biologically active substance and the surface may be coated with this mixture.

The photoactivable heterobifunctional coupling agents carry different functional groups at each end of the molecule and may be of varied molecular size. One is selectively reactive with the biologically active substance while the other is a group capable of being photoactivated, preferably an aryldiazirine or alkyldiazirine group. The group which is reactive with the biologically active substance may be especially an isothiocyanate group capable of reacting with primary amines or a succinimidyloxy ester functional group capable of reacting with primary amines, or a malcimido group whose double bond can react with thiols by an addition reaction. Activated esters and anhydrides easily react with a hydroxyl or amino group in an organic solvent or an organic solvent-buffer mixture, if need be in the presence of a condensation catalyst.

The expression "biologically active substance" (BAS in abbreviation) is to be understood in a broad sense and includes especially synthetic or natural substances of low molecular weight, such as phospholipids, glycolipids, oligo- and monosaccharides, amino acids, peptides, oligonucleotides, medications or metabolites. It may also be natural or synthetic macromolecules of high molecular weight, such as proteins, enzymes, antigens, haptens, antibodies, receptors, cell bonding proteins, polycarbohydrates or complex biological structures such as viruses, organelles, cells, bacteria or tissue sections. As indicated above, these substances may be modified by the coupling agent before the surface is coated or may be immobilized on the surface after the photoimmobilization of said agent on the surface.

The BAS may advantageously be immobilized in the form of a substantially monomolecular layer by suitably regulating the number of molecules of the coupling agent which are bound to the substrate by the photochemical process. This mixture may be obtained by modifying the concentration of the coupling agent applied to the substrate and the conditions of exposure to the radiation (time, intensity).

The exposure to the radiation which activates the carbene-generating functional group may be performed overall on a material surface or photopatterned using appropriate masks.

The source of light must emit radiations whose wavelength(s) overlap the absorption band of the functional group of the coupling agent which is capable of being photoactivated. In the case of aryldiazirines a light source emitting at 350±30 nm has been found to be satisfactory. It is advantageous, in any event, to employ radiation of wavelengths longer than 320 nm to avoid possible detrimental effects on the BAS. Examples of appropriate sources are suitably filtered sunlight, polarized light, the light from a commercially available source like the Stratalinker® device, high-pressure mercury lamps, lasers and the like.

An exposure according to a pattern can be obtained with the aid of an appropriate mask or by "writing" with a laser.

The device of the invention may be, by way of example without any limitation being implied, a biosensor, a bioreactor, an implant, a device for medical or industrial analysis or a device for diagnosis.

The following nonlimiting examples are given to illustrate the invention.

In the examples the following general three-stage operating procedure is used:

Stage 1: the bifunctional coupling agent capable of being photoactivated or the product of the reaction between the BAS and the coupling agent is applied as a coating to a clean surface of the substrate.

Stage 2: the coated surface is irradiated with the light source either overall or by mask-assisted patterning.

Stage 3: the molecules which are not immobilized during Stage 2 are removed by washing.

The coating may be produced by application and drying, by physical adsorption or by sedimentation aided by centrifuging, and the like.

The following abbreviations are employed in these examples:

| | |
|---|---|
| BSA | bovine serum albumin |
| GOD | glucose oxidase |
| HEPLS | 4-(2-hydroxyethyl)piperazine-1-ethane- sulfonic acid (supplied by Sigma company) |
| MAD | N-{m-[(3-trifluoromethyl)diazirin-3-yl]phenyl}-4-maleimidobutyramide (prepared as described by Collioud et al., Bioconjugate Chem. 4, 428–436 (1993). |
| PBS | phosphate buffer saline solution (150 mM NaCl, 5 mM sodium phosphate buffer, pH 7.4) |
| SFM | scanning atomic force microscopy |
| T-BSA | bovine serum albumin modified with 3-(trifluoromethyl)-3-(m-isothiocyanatophenyl)diazirin (synthesized as described by Gao et al., Biotech. Appl. Biochem. 20, 251–263 (1994). |
| T-GOD | glucose oxidase modified with 3-(trifluoromethyl)-3-(m-isothiocyanatophenyl)diazirin |
| TRIMID | 3-(trifluoromethyl)-3-(m-isothiocyanato-phenyl)diazirin (prepared as described by Dolder et al., J. Prot. Chem., 9, 407–415 (1990). |

Sources of reactive derivatives

| | |
|---|---|
| [$^{14}$C]-HCOH, specified radioactivity of 53 mCi mmol$^{-1}$ | |
| | New England Nuclear - |
| [$^{35}$S]-cysteine, specified activity of 20 to 150 mCl mmol$^{-1}$) Amersham | |
| Immunologically pure monoclonal mouse IgG | |
| | Pierce |
| Monoclonal mouse anti-dinitrophenyl (DNP) antibody | |
| | Sigma |
| Glucose oxidase | |
| | Sigma (β-D-glucose: oxygen 1-oxidoreductase EC 1.1.3.4. *Aspergillus niger*) |
| PD10 Column | prepacked chromatography column bought from Pharmacia |
| Photomasks | nickel photomasks with 300 μm × 15 mm slits at 500 μm intervals and with 20 μm × 15 mm slits at 180 μm intervals, supplied by Towne Laboratories Inc., Somerville, N.J., U.S.A. |

-continued

| | |
|---|---|
| Si chips, coated with silicon nitride | |
| | Si chips ([100] orientation, p type) comprising a 100 nm layer of thermal oxide and a 200 nm layer of silicon nitride produced in the precut state (5 × 5 mm) to order by the Institute of Microtechnology, University of Neuchatel, Switzerland |
| Levers for SFM | Pyramidal cantilevers and levers made of silicon nitride were obtained from Park Scientific Instruments, Sunnyvale CA, USA |

Light sources:

| | |
|---|---|
| Stratalinker | U.V. crosslinker Stratalinker 2400 (Stratagene Gmbl l, Heidelberg, Germany) fitted with 5 bulbs (F158 BL, 15W black light). |
| Argon laser | laser fitted with a UV mirror (multiline at 351–363 nm). |
| Light intensity measurement | |
| | the irradiation dose was measured with a Suss intensitometer model 1000 with a P 320 nm detection cell. |

EXAMPLE 1

Binding of N-m-[(3-trifluoromethyl)diazirin-3-yl (phenyl)]- 4-maleimidobutyramide (MAD) to silicon nitride Si chips coated with silicon nitride were rinsed and treated with ultrasound in acetone three times for 15 minutes and once in isopropanol for 15 minutes to remove the protective photosensitive coating. The chips were then vacuum-dried for 60 minutes (5 mbar at ambient temperature). MAD (10 μl, 1 mM in ethanol) was applied to the surface of the silicon nitride. The chips were vacuum-dried for 30 minutes (5 mbar at ambient temperature). The chips were exposed to an activating light (Stratalinker® light source, 350 nanometers, 20 minutes, 0.7 mW cm$^2$) through masks with a slit pattern (300 μm and 20 μm). After exposure to the light the chips were washed and treated with ultrasound three times for 10 minutes in chloroform and once in ethanol. The substrate was then incubated for two hours at ambient temperature with 1 μl of [$^{35}$S]-cysteine (15 μCi) in 80 μl of solvent consisting of 0.1M, sodium phosphate buffer pH 6.8, and of ethanol (3/1 v/v). The modified surface was rinsed with ethanol and was treated with ultrasound (2 minutes) in 0.1M, sodium phosphate buffer pH 6.8. After drying, a radiography film (Hyper film, Amersham) was exposed to the treated surface for 2 days to obtain an image of the radioactive regions. A pattern was obtained with bands corresponding to the mask slits.

EXAMPLE 2

Photoimmobilization according to a pattern of T-BSA on silicon nitride

Si chips coated with silicon nitride were cleaned and pretreated as in Example 1 above. T-BSA (10 μl of a solution containing 610 μg of protein per ml in a 1.5 mM NaCl, 0.5 mM Na phosphate buffer pH 7.4) was deposited on the silicon nitride surface and dried at reduced pressure (2 hours, 5 mbar). The irradiation was performed through a mask with a 20 μm slit pattern with the Stratalinker light source for 20 minutes and at an irradiance of 0.7 mW cm$^{-2}$. The clips were then washed and treated with ultrasound three times for 15 minutes in a 1.5 mM NaCl, 0.05mM sodium phosphate buffer pH 7.4 containing 0.02% of Tween®. For the atomic force microscopy (AlM) study the chips with 20 μm patterns were mounted in the liquid cell of the atomic force microscope. After addition of PBS, the system was allowed to equilibrate for 60 minutes before imaging by scanning atomic force microscopy. Here, too, a pattern corresponding to that of the mask with slits was obtained.

EXAMPLE 3

Immobilization of immunological reagents

Preparation of mouse immunoglobulin (lgG) radio tagged with $^{14}$C. Mouse lgG (1 mg in 500 µl of 100 mM, sodium phosphate buffer pH 6.8) was transferred to 0.1M, HLPLS buffer pH 7.5 by chromatography on a PD10 chromatography column. 29.7 µl (1 µmol, 53 µCi) of [$^{14}$C]-formaldehyde and 65 µmol of sodium cyanoborohydride were then added to the protein collected (890 µg in 1.5 ml of HEPES buffer) and the reaction mixture was stirred for 4 hours at ambient temperature in the dark. The [$^{14}$C]-methylated mouse lgG was isolated from the reaction mixture by chromatography on PD10 in 0.1M, sodium phosphate buffer pH 6.8. Specific radioactivity was determined by scintillation counting and the protein concentrations were determined by measuring the absorption at 280 nanometers ($A^{1\%}$—14.0). The modified antibodies were stored at −20° C.

Photoimmobilization of the antibodies on chips coated with silicon nitride

The antibodies were mixed with T-BSA (with BSA in the case of the control samples) in a weight ratio of ¼. Samples containing 0.25 µg of antibody and 1.0 µg of T-BSA were adjusted to a final volume of 25 µl (in 0.01M, sodium phosphate buffer pH 6.8) and applied to the surface of 5×5 mm chips. The chips were placed in the wells of a Falcon multiwell plate. After drying at reduced pressure (2 mbar) at ambient temperature the coated chips were irradiated for 20 minutes. A Stratalinker 2400 (Stratagene GmbH, Heidelberg) device for ultraviolet crosslinking, equipped with 5 bulbs (F158 BL, 15W black light) was employed for activating the photolabel. The samples were placed at a distance of 4 cm from the light source and exposed to a radiation dose of 0.7 mW cm$^{-2}$ (Suss model 1000 intenisitometer with a 320 nanometer detection cell). The chips with silicon nitride were agitated perpendicularly to the bulbs with a swing of 4 cm and at a frequency of 26 cycles per minute. Samples treated in an identical manner and not irradiated were used as control. The modified chips were washed with PBS containing 0.02% of Tween 20 (3×500 µl/chip) and distilled water (3×500 µl/chip). The determination of the photoimmobilized antibodies was performed with the $^{14}$-radiolabeled antibodies. It was thus determined that approximately 20% of the antibodies applied were photoimmobilized on the silicon nitride surface.

EXAMPLE 4

Covalent coupling of glucose oxidase to silicon nitride

Before the photoimmobilization on silicon nitride surfaces the glucose oxidase enzyme (β-D-glucose:oxygen 1-oxidoreductase, EC 1.1.3.4.) was modified with TRIMID). Briefly, GOD (81 mg) and β-D-glucose (1.27 g) were dissolved in 0.1% triethylamine pH 11.4, the final pH of the solution was adjusted to pH 10.4 with pure triothylamine. TRIMID (170µl, 29µmol in chloroform) was added and the mixture was subjected to ultrasonic treatment for 30 seconds. After incubation of the reaction mixture with stirring for 2 hours at 37° C. the mixture was chromatographed on Sephadex G25 in a 1.5 mM NaCl, 0.05 mM sodium phosphate, buffer pH 7.4. The first fractions eluted were collected and analyzed for protein content and their enzymatic activity. The specific enzymatic activity of the glucose oxidase modified with TRIMID (T-GOD) was 0.6 to 1 unit per milligram of protein. The content of covalently bonded photoreagent was 8±2 moles of TRIMID per mole of GOD. T-GOD (25 µl containing 2 µg of T-GOD in a 1.5 mM NaCl, 0.05 mM sodium phosphate, buffer pH 7.4) was deposited on chips coated with polished silicon nitride and was dried at reduced pressure at ambient temperature. Samples were irradiated with the Stratalinker light source for 40 minutes. The samples exposed to the light and unirradiated samples were then washed with PBS containing 0.02% of Tween 20 (3×500 µl/chip) and with bidistilled water (3×500 µl/chip). The activity of the glucose oxidase retained on the chips was determined by the spectrophotometric method described by Foulds et al. (1990), *Immunoelectrodes in Biosensors. A practical Approach*, CASS, A.L.G. ed., IRL Press, Oxford. The determination is based on a peroxidase indicator reaction which measures the hydrogen peroxide released in the enzymatic reaction. This particular determination is based on the oxidative coupling of hydrogen peroxide with 4-aminiophenazone and a phenol in the presence of horse radish peroxidase, to form a chromogen (a quinoneimine-type dye) with a maximum absorption at 520 nanometers. The measured enzymatic activities were as follows:

| Sample | Enzymatic activity of the GOD (absorption 520 nm) |
|---|---|
| Photoimmobilized GOD | 0.48 |
| Control | 0.003 |

Studies performed with radiolabeled T-GOD showed that 5% of the enzyme applied was retained on the surface after photoimmobilization. This corresponds to 100 nanograms per 25 mm$^2$.

EXAMPLE 5

Covalent functionalization with an antibody of a tip for scanning force microscopy Cantilevers for scanning force microscopy were cleaned by ultrasonic treatment in acetone three times for 15 minutes and in isopropanol once for 15 minutes. 5 µl of MAD (100 µM in ethanol) were deposited three times on the cantilever tip, the tip being left to dry in air between the applications. The samples were placed in the Stratalinker apparatus at a distance of 4 cm from the light source and exposed for 20 minutes to an irradiance of 0.7 mW cm$^{-2}$. Alternatively, the cantilever tip was activated for 60 seconds with a focused argon (354 µm) laser (50 µm beam diameter) with an irradiation dose of 130 mW cm$^{-2}$. The photoactivated cantilever tips were rinsed and treated with ultrasound three times for 1 minute in ethanol. The cantilever tips were then soaked in a freshly prepared solution containing F(ab') fragments (100 µl, 51 µg of protein) in 0.1M sodium acetate, 0.5M sodium chloride and 1 mM EDTA, pH 5.0, and left to incubate for 12 hours at 37° C. F(ab')$_2$ fragments of a mouse antibody, labeled with fluorescein isothiocyanate were employed to demonstrate the binding of the antibody to the tip. The fluorescein-labeled F(ab')$_2$ fragments were treated with dithiothreitol. The reducing agent was removed by chromatography on a PD10 column and the F(ab') fragments were immobilized thermochemically on tips functionalized with MAD. The cantilever tips were then rinsed and were treated with ultrasound in a 0.1M sodium phosphate buffer pH 6.0, and were left to equilibrate in this buffer for 2 hours. The binding of the antibody fragments to the tip by MAD was visualized using fluorescence microscopy.

We claim:

1. A device including an inorganic substrate and at least one biologically active substance bound to at least a part of the surface of said substrate, said device being obtained by simultaneous or sequential reacting of said substrate and of said substance with a bifunctional coupling agent in which one of the functional groups has been photoactivated to generate carbenes that covalently bind the coupling agent to the inorganic substrate, and the other functional group binds the coupling agent to the biologically active substance, said substrate being a covalent inorganic nitride.

2. The device as claimed in claim 1, wherein said substrate is silicon nitride.

3. The device as claimed in claim 2, wherein the silicon nitride is in the form of a layer coating a chip or wafer of semiconductor silicon.

4. The device as claimed in claim 1, wherein the functional group of the coupling agent which is capable of being photoactivated is a carbene-generating diazirin functional group.

5. The device as claimed in claim 1, wherein the reaction of the carbene-generating functional group is activated by exposure to light through a mask having a determined pattern so that the biologically active substance is bound to the substrate according to a pattern of a shape corresponding to that of the mask pattern.

6. The device as claimed in claim 1, wherein the bound biologically active substance forms a substantially monomolecular layer.

7. The device as claimed in claim 1, wherein the biologically active substance is selected from the group consisting of ligands, antigens, haptens, antibodies, receptors, enzymes, organelles, cells, viruses, bacteria, tissues, proteins, glycoproteins, phospholipids, glycolipids, oligo- and monosaccharides, polycarbohydrates, cell binding proteins, amino acids, peptides, oligonucleotides, medications and metabolites.

8. The device as claimed in claim 1, which is a biosensor, a bioreactor, an implant, a device for medical or industrial analysis or a device for diagnosis.

9. A method for binding a biologically active substance to a covalent inorganic nitride surface of a substrate, comprising the steps of reacting said surface with a bifunctional coupling agent by photoactivating one of the functional groups of said coupling agent to generate carbenes for covalently binding the coupling agent to said surface, and binding the biologically active substance to said coupling agent by the other functional group of said coupling agent.

* * * * *